United States Patent
Chang et al.

(10) Patent No.: US 9,080,219 B2
(45) Date of Patent: Jul. 14, 2015

(54) BACILLUS AMYLOLIQUEFACIENS K317 FOR SUPPRESSING THE GROWTH OF ANTIBIOTICS-RESISTANT PATHOGENIC MICROORGANISM OR ENTEROPATHOGENIC MICROORGANISM

(75) Inventors: Young-Hyo Chang, Taejeon-si (KR); Min Young Jung, Suncheon-si (KR); Moon-Soo Rhee, Taejeon-si (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 898 days.

(21) Appl. No.: 12/530,616

(22) PCT Filed: Nov. 26, 2007

(86) PCT No.: PCT/KR2007/005985
§ 371 (c)(1),
(2), (4) Date: Sep. 9, 2009

(87) PCT Pub. No.: WO2008/111719
PCT Pub. Date: Sep. 18, 2008

(65) Prior Publication Data
US 2010/0021576 A1    Jan. 28, 2010

(30) Foreign Application Priority Data
Mar. 13, 2007   (KR) .................. 10-2007-0024566

(51) Int. Cl.
| | |
|---|---|
| *A61K 35/742* | (2015.01) |
| *A61K 35/74* | (2006.01) |
| *A61K 9/20* | (2006.01) |
| *C12R 1/07* | (2006.01) |
| *A23L 1/30* | (2006.01) |
| *C12P 1/04* | (2006.01) |

(52) U.S. Cl.
CPC ............... *C12R 1/07* (2013.01); *A23L 1/3014* (2013.01); *A61K 35/742* (2013.01); *C12P 1/04* (2013.01)

(58) Field of Classification Search
IPC .................................. A61K 35/742,35/74, 9/20
See application file for complete search history.

(56) References Cited

FOREIGN PATENT DOCUMENTS

| | | |
|---|---|---|
| KR | 12-020051803 A | 6/2002 |
| KR | 10-030002398 A | 1/2003 |
| KR | 10-0427600 B1 | 4/2004 |

OTHER PUBLICATIONS

NCBI GenBank Accession No. DQ422953 'Bacillus amyloliquefaciens strain Ba-74501 16S ribosomal RNA gene, partial sequence' Mar. 26, 2006, one page.*

(Continued)

*Primary Examiner* — Patricia A Leith
(74) *Attorney, Agent, or Firm* — Lathrop & Gage LLP

(57) ABSTRACT

The present invention relates to a *Bacillus amyloliquefaciens* K317 strain suppressing the growth of antibiotics-resistant pathogenic microorganisms or enteropathogenic microorganisms, more precisely a *Bacillus amyloliquefaciens* K317 strain, a culture supernatant thereof and an antibacterial metabolite separated from the same. The *Bacillus amyloliquefaciens* K317 strain, the culture supernatant thereof and the antibacterial metabolite separated from the same of the invention can be effectively used for the composition, health food, and probiotics for inhibiting the growth of antibiotics-resistant pathogenic microorganisms and enteropathogenic microorganisms, since they have excellent antibacterial activity and inhibition effect on the growth of methicillin resistant pathogenic microorganism and such enteropathogenic microorganism as *Edwardsiella tarda, E. coli* and *Staphylococcus epidermidis*.

15 Claims, 13 Drawing Sheets

The clear zone formed by inhibiting MRSA

(56) References Cited

OTHER PUBLICATIONS

Morita et al. (2001) "Antibacterial Activity of *Bacillus amyloliquefaciens* Phage Endolysin without Holin Conjugation," *Journal of Bioscience and Bioengineering*, 2001, vol. 91, No. 5, pp. 469-473.

NCBI Genbank Accession No. DQ422953, Mar. 26, 2006.
International Search Report for PCT/KR2007/005985 dated Feb. 26, 2008.
Written Opinion of the International Searching Authority for PCT/KR2007/005985 dated Feb. 26, 2008.

* cited by examiner

The clear zone formed by inhibiting MRSA

The early stage of co-culture yellow : MRSA
white : K317

24 hours after co-culture

SEQUENCE LISTING

<160> NUMBER OF SEQ ID NOS: 3

<210> SEQ ID NO 1
<211> LENGTH: 19
<212> TYPE: DNA
<213> ORGANISM: Artificial
<220> FEATURE:
<223> OTHER INFORMATION: forward primer

<400> SEQUENCE: 1
gagtttgatc ctggctcag                                                    19

<210> SEQ ID NO 2
<211> LENGTH: 19
<212> TYPE: DNA
<213> ORGANISM: Artificial
<220> FEATURE:
<223> OTHER INFORMATION: reverse primer

<400> SEQUENCE: 2
ggttaccttg ttacgactt                                                    19

<210> SEQ ID NO 3
<211> LENGTH: 1389
<212> TYPE: DNA
<213> ORGANISM: Artificial
<220> FEATURE:
<223> OTHER INFORMATION: 16S rRNA sequence

<400> SEQUENCE: 3
ggacagatgg gagcttgctc cctgatgtta gcggcggacg ggtgagtaac acgtgggtaa      60
cctgcctgta agactgggat aactccggga aaccggggct aataccggat ggttgtctga     120
accgcatggt tcagacataa aaggtggctt cggctaccac ttacagatgg acccgcggcg     180
cattagctag ttggtgaggt aacggctcac caaggcgacg atgcgtagcc gacctgagag     240
ggtgatcggc cacactggga ctgagacacg gcccagactc ctacgggagg cagcagtagg     300
gaatcttccg caatggacga aagtctgacg agcaacgcc gcgtgagtga tgaaggtttt     360
cggatcgtaa agctctgttg ttagggaaga acaagtgccg ttcaaatagg gcggcacctt     420
gacggtacct aaccagaaag ccacggctaa ctacgtgcca gcagccgcgg taatacgtag     480
gtggcaagcg ttgtccggaa ttattgggcg taaagggctc gcaggcggtt tcttaagtct     540
gatgtgaaag cccccggctc aaccggggag ggtcattgga aactgggaa cttgagtgca     600 gaagaggaga gtggaattcc acgtgtagcg gtgaaatgcg tagagatgtg gaggaacacc     660
agtggcgaag gcgactctct ggtctgtaac tgacgctgag gagcgaaagc gtggggagcg     720
aacaggatta gataccctgg tagtccacgc cgtaaacgat gagtgctaag tgttaggggg     780
tttccgcccc ttagtgctgc agctaacgca ttaagcactc cgcctgggga gtacggtcgc     840
aagactgaaa ctcaaaggaa ttgacggggg cccgcacaag cggtggagca tgtggtttaa     900
ttcgaagcaa cgcgaagaac cttaccaggt cttgacatcc tctgacaatc ctagagatag     960
gacgtcccct cggggggcag agtgacaggt ggtgcatggt tgtcgtcagc tcgtgtcgtg    1020
agatgttggg ttaagtcccg caacgagcgc aacccttgat cttagttgcc agcattcagt    1080
tgggcactct aaggtgactg ccggtgacaa accgaggaa ggtggggatg acgtcaaatc     1140
atcatgcccc ttatgacctg gctacacac gtgctacaat ggacagaaca aagggcagcg     1200
aaaccgcgag gttaagccaa tcccacaaat ctgttctcag ttcggatcgc agtctgcaac    1260
tcgactgcgt gaagctggaa tcgctagtaa tcgcggatca gcatgccgcg gtgaatacgt    1320

```
tcccgggcct tgtacacacc gcccgtcaca ccacgagagt ttgtaacacc cgaagtcggt    1380
gaggtaacc                                                            1389
```

BACILLUS AMYLOLIQUEFACIENS K317 FOR SUPPRESSING THE GROWTH OF ANTIBIOTICS-RESISTANT PATHOGENIC MICROORGANISM OR ENTEROPATHOGENIC MICROORGANISM

CROSS-REFERENCE TO RELATED APPLICATIONS

This application is the U.S. National Stage of International Application No. PCT/KR2007/005985, filed Nov. 26, 2007, which claims the benefit of Korean Patent Application No. 10-2007-0024566, filed Mar. 13, 2007, both of which are hereby incorporated by reference to the extent not inconsistent with the disclosure herewith.

TECHNICAL FIELD

The present invention relates to a *Bacillus amyloliquefaciens* K317 strain suppressing the growth of antibiotics-resistant pathogenic microorganisms or enteropathogenic microorganisms, more precisely a *Bacillus amyloliquefaciens* K317 strain, a culture supernatant thereof and an antibacterial metabolite separated from the same.

BACKGROUND ART

Among many pathogenic microorganisms, the one casing trouble most over the world is *Staphylococcus aureus*, which is a Gram-positive coccus detected in approximately 30% of the total earth population and is known as a pathogen causing nosocomial infection (Isabel C. V, Robert S. K., Francisco A. K., *J. Am. Acad. Dermatol.* 50:845-849, 2004). This bacterium causes infection primarily on skin and soft tissue, leading to pyoderma, and further induces systemic infection threatening a life such as osteomyelitis, endocarditis, sepsis and bacteremia (Henry Shinefield, M. D. et al., *The New England J. of Med.* 346:491-496, 2002). Antibacterial agents for *Staphylococcus aureus* such as penicillin and methicillin have been used as a therapeutic agent for the infection over decades owing to their excellent antibacterial effect. However, since the strain exhibiting methicillin resistance (methicillin-resistant *Staphylococcus aureus*: MRSA) was first reported in England in 1961, the number of such antibiotics-resistant strains has been increasing (Standing Medical Advisory Committee, Department of Health, 1998).

The appearance of antibiotics resistant strains resulted from reckless overuse of antibiotics is also a serious problem in Korea. For example, the population of methicillin resistant strains reaches around 50% and according to the recent investigation by Korean Society for Nosocomial Infection Control, the rate of MRSA strains separated from most university hospitals and general hospitals reaches 70-80%. Therefore, it is required to develop a sanitary, safe and effective therapeutic agent for MRSA.

Korean Patent Application No. 2004-55648 describes that *Streptomyces laidlogenes* DS684 isolated from soil has the inhibitory effect on methicillin and vancomycin resistant strains, and Korean Patent No. 654370 describes that *Lactobacillus ruminus* SPM0211 has the inhibitory effect on vancomycin resistant strains.

Probiotics indicate the microorganism balancing intestinal microflora, the microorganism having antibacterial and enzyme activities and the product produced by the same (Fuller, R. *J Appl Bacteriol.* 66(5):365-378, 1989). Probiotics are also defined as live bacteria in the form of single strain or combined strains which can be supplied to human or animals in the form of dried cells or fermented products to improve intestinal microflora. Therefore, the probiotics use human intestines as a habitat and need to survive until they reach intestines as non-pathogenic and non-toxic. Further, the probiotics have to maintain the survival rate and activity in the product carrying the probiotics until they are consumed and have to be sensitive to antibiotics used for the prevention of infection and at the same time must not contain antibiotics resistant plasmid. Besides, the probiotics have to have resistance against acid, enzyme and bile in intestines (Mishra, C. et al., *Asia Pacific J Clin Nutr.* 5:20-24, 1996).

Probiotics are exemplified by *Bacillus* sp. having excellent digestive enzyme (amylase, protease, lipase, cellulose and phosphatase) producing capacity, *Lactobacillus* sp. capable of decomposing low molecular carbohydrates by producing organic acid, *Saccharomyces* sp. facilitating absorption in intestine after converting into lactic acid and vitamin B synthesis and vitamin E absorption as well, and Photosynthetic bacteria suppressing foul smell by metabolizing malodorous substances (ammonia, hydrogen sulfide, amines, etc.) remaining in feces of cattle.

In particular, *Bacillus* sp. and *Lactobacillus* sp. are generally called lactic acid bacteria (LAB) and separated from food. These species include strains that produce antibacterial substances working against saprogenic bacteria to prevent food from being rotten, which makes them very valuable probiotics (Tagg, G. U. et al., *Bacteriol. Rev.* 40:772-756, 1976). These lactic acid bacteria produce antibacterial peptide, so called bacteriocin, having antibacterial mechanism which has nothing to do with antibiotics resistance mechanism. Bacteriocin is not like the conventional antibiotics and is difficult to be defined precisely, since bacteriocin is not typical in molecular weight, biochemical characteristics, antibacterial spectrum to host or mechanisms. Klaenhammer defined bacteriocin as protein or protein complex that has antibacterial activity direct to those species close to bacteriocin producing bacteria (Klaenhammer, T R. *Biochimie* 70:337-379, 1998). The substances having antibacterial activity are suggested as "bacteriocin-like substances" even though they are not the typical ones identified according to the standard (Tagg, G. U. et al., *Bacteriol. Rev.* 40:772-756, 1976). There is no boundary fixed among antibiotics, bacteriocins and microcins, but bacteriocins are classified into bacteriostatics or bacteriocidals according to their activity spectrum and belong to peptide antibiotics group. Antibiotics are produced by non-ribosomal synthesis based on several steps of enzymatic mechanism. In the meantime, bacteriocins are generated by ribosomal synthesis and rarely have resistance but seem to have potential for resistance (Hurst A. *Adv Appl Microbiol* 27:85-123, 1981; Harvis, B., Farr, J. Biochim Biophys Acta 227:232-340, 1971; Harris, L J. et al., *J Food Prot* 52:384-387, 1989). Lots of antibiotics can be chemically synthesized but no chemical synthesis of bacteriocins has been reported, yet. With the advancement of genetic engineering techniques, bacteriocin-like substances can be reconstructed and recombinated, precisely lipids or carbohydrates take a part of bacteriocin complex. Bacteriocin can be adhered on cells or released out of the cells, can be generated before and after growth cycle, has resistance against such enzymes as protease, and is stable against pH and temperature. Antibacterial mechanism of bacteriocin has not been disclosed, yet, and only thing that has been reported is that bacteriocin is stuck in cell membrane channel to induce cell lysis. Cell lysis is directly associated with cell death and depends on sensitive bacteria having non-specific receptor site and specific receptor site (Bhunia, A K. et al., *J Appl Bacteriol* 57:492-498, 1991). Bacteriocin with these characteristics is rising as alternative antibiotics and is acknowledged as a safe antibacterial agent used as a food preservative.

*Bacillus* is a very interesting and industrially important species applicable in various industries, particularly regarding antibacterial activity, because it can produce numbers of peptide antibiotics and is safe for food and industrial use (Paik, H. D. et al., *J. Ind. Microbiol. Biotechnol.* 19:294-298, 1997). It has been known that many *Bacillus* species such as *Bacillus cereus, Bacillus subtilis* and *Bacillus thuringiensis* produce bacteriocins and bacteriocin-like substances (Paik, H. D. et al., *J. Ind. Microbiol. Biotechnol.* 19:294-298, 1997; Zheng, G. et al., *J. Bacteriol.* 181:7346-7355, 1999; Bizani, D., Brandelli, A. *J. Appl. Microbiol.* 93:512-519, 2002).

The present inventors separated the novel *Bacillus amyloliquefaciens* K317 strain (KCTC 11042BP) from Kimchi, the Korean traditional safe fermented food, and further completed this invention by confirming that the culture solution of the strain and the antibacterial metabolite separated therefrom had strong inhibitory effect on various pathogenic enterobacteria including 30 kinds of MRSA strains.

DISCLOSURE

Technical Problem

It is an object of the present invention to provide a novel strain inhibiting the growth of antibiotics-resistant pathogenic microorganisms or enteropathogenic microorganisms, a supernatant of the culture solution thereof, and an antibacterial metabolite isolated from the same.

Technical Solution

To achieve the above object, the present invention provides a *Bacillus amyloliquefaciens* K317 strain suppressing the growth of antibiotics-resistant pathogenic microorganisms or enteropathogenic microorganisms.

The present invention also provides a supernatant of the culture solution of *Bacillus amyloliquefaciens* K317.

The present invention further provides an antibacterial metabolite isolated from the supernatant of the culture solution of *Bacillus amyloliquefaciens* K317.

The present invention also provides probiotics comprising the above strain, the culture supernatant or the antibacterial metabolite as an active ingredient.

The present invention also provides a composition for inhibiting the growth of antibiotics-resistant pathogenic microorganisms or enteropathogenic microorganisms which comprises the above strain, the culture supernatant or the antibacterial metabolite as an active ingredient.

The present invention also provides health food for inhibiting the growth of antibiotics-resistant pathogenic microorganisms or enteropathogenic microorganisms comprising *Bacillus amyloliquefaciens* K317, the culture supernatant thereof or the antibacterial metabolite as an active ingredient.

The present invention also provides a feed additive for inhibiting the growth of antibiotics-resistant pathogenic microorganisms or enteropathogenic microorganisms comprising *Bacillus amyloliquefaciens* K317, the culture supernatant thereof or the antibacterial metabolite as an active ingredient.

Advantageous Effect

The novel *Bacillus amyloliquefaciens* K317 strain, the supernatant of the culture thereof and the antibacterial metabolite recovered from the same of the present invention can inhibit the growth of antibiotics-resistant pathogenic microorganisms including MRSA strain and enteropathogenic microorganisms effectively, so that they can be used for the composition or health food and as probiotics for inhibiting the growth of such pathogenic microorganisms.

DESCRIPTION OF DRAWINGS

The application of the preferred embodiments of the present invention is best understood with reference to the accompanying drawings, wherein.

BEST MODE

Figure 1:
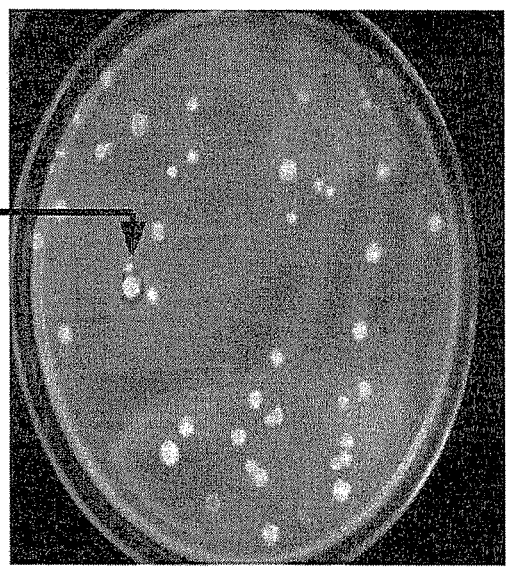
FIG. 1 illustrates the result of growth inhibiting test with antibiotics-resistant pathogenic microorganisms to isolate *Bacillus amyloliquefaciens* K317.
Figure 1:
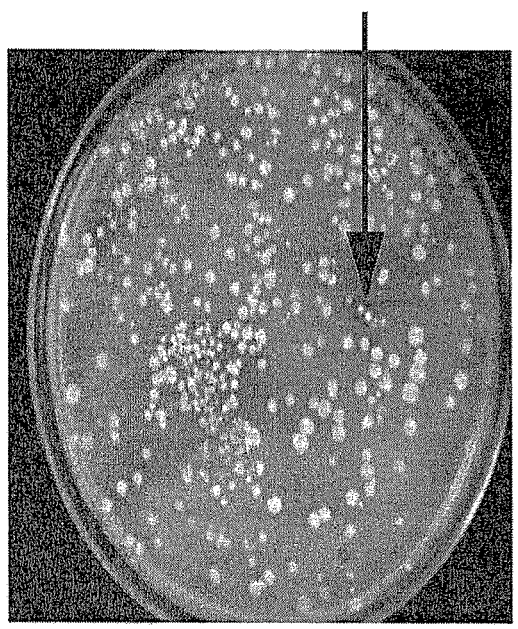

Hereinafter, the present invention is described in detail.

To select a microorganism exhibiting antibacterial activity against MRSA (methicillin-resistant *Stapylococcus aureus*), the antibiotics-resistant pathogenic microorganism, the present inventors diluted Kimchi juice in the plate on which MRSA strains were smeared, followed by culture. Colonies having clear zones were selected (see FIG. 1). The selected colonies were separated and purified and the strain identified at last was named *Bacillus* sp. K317, which was deposited, in accordance with the Budapest Treaty, at Korean Collection for Type Cultures, Korea Research Institute of Bioscience and Biotechnology located at Yuseong-Gu, Daejeon, Korea, on Dec. 4, 2006 (Accession No: KCTC 11042BP). This strain deposit will be maintained without restriction in the KCTC depository for a period of 30 years, or 5 years after the last request, or for the effective life of the patent, whichever is longer, and will be replaced if the deposit becomes non-viable during that period. Upon grant of a patent, all restrictions imposed by the depositor on the availability to the public of the deposited biological material will be irrevocably removed.

To investigate the inhibiting activity of the strain of the invention on the growth of pathogenic microorganisms, the present inventors cultured *Salmonella typhimurium, Edwardsiella tarda, E. coli, Staphylococcus epidermidis* distributed from Korean Collection for Type Cultures (KCTC), Korea Research Institute of Bioscience and Biotechnology (KRIBB) and 30 strains of MRSA, the antibiotics-resistant bacteria, distributed from Culture Collection of Antimicrobial Resistant Microbes, Seoul Women's University, Seoul, Korea, in proper media, which were then smeared on MH media with fixed numbers of live cells. The *Bacillus amyloliquefaciens* K317 strain was streaked on the media and cultured. Then, the formation of clear zone was observed. As a result, clear zone was observed around streaking of *Bacillus amyloliquefaciens* K317, indicating that the growth of enteropathogenic microorganisms was suppressed (see FIG. 3). *Bacillus amyloliquefaciens* K317 was co-cultured with MRSA. As a result, in the early stage of co-culture, both MRSA and *Bacillus amyloliquefaciens* K317 formed colonies, but after 24 hours of the co-culture, MRSA did not form a colony anymore (see FIG. 4). The above results indicate that the *Bacillus amyloliquefaciens* K317 of the present invention inhibits the growth of the antibiotics-resistant pathogenic microorganism MRSA and enteropathogenic microorganisms effectively.

The present invention also provides a supernatant of the culture solution of *Bacillus amyloliquefaciens* K317.

The present inventors diluted the supernatant of *Bacillus amyloliquefaciens* K317 culture solution, followed by investigating the inhibitory effect on pathogenic microorganisms. The target strains for the experiment were *Salmonella typhimurium, Edwardsiella tarda, E. coli, Staphylococcus epidermidis* and 30 strains of MRSA, the antibiotics-resistant bacteria.

Figure 5:
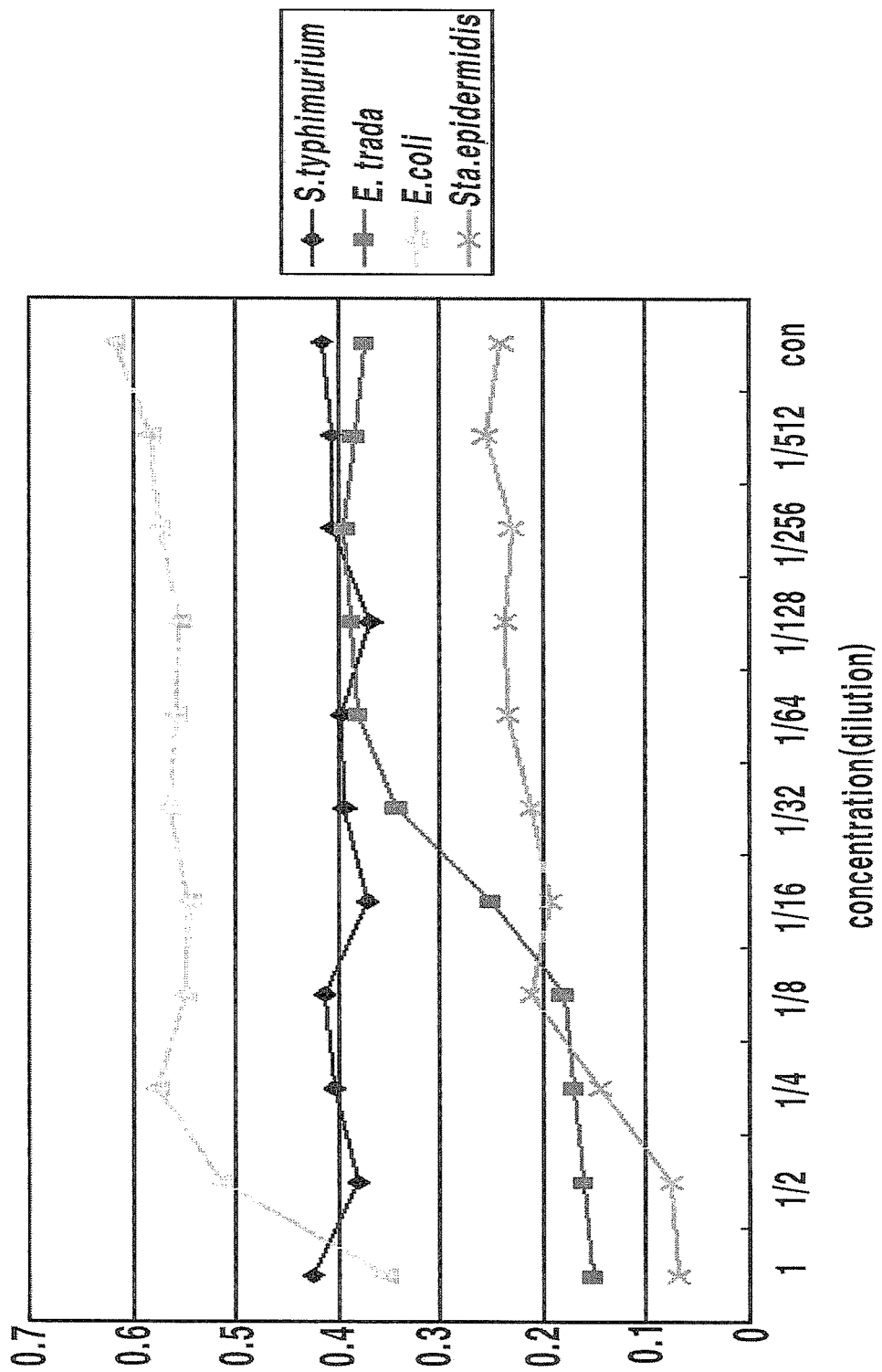
FIG. 5 is a graph illustrating the growth inhibition of enteropathogenic microorganism according to the diluted concentrations of the supernatant of *Bacillus amyloliquefaciens* K317 culture solution.
Figure 6:
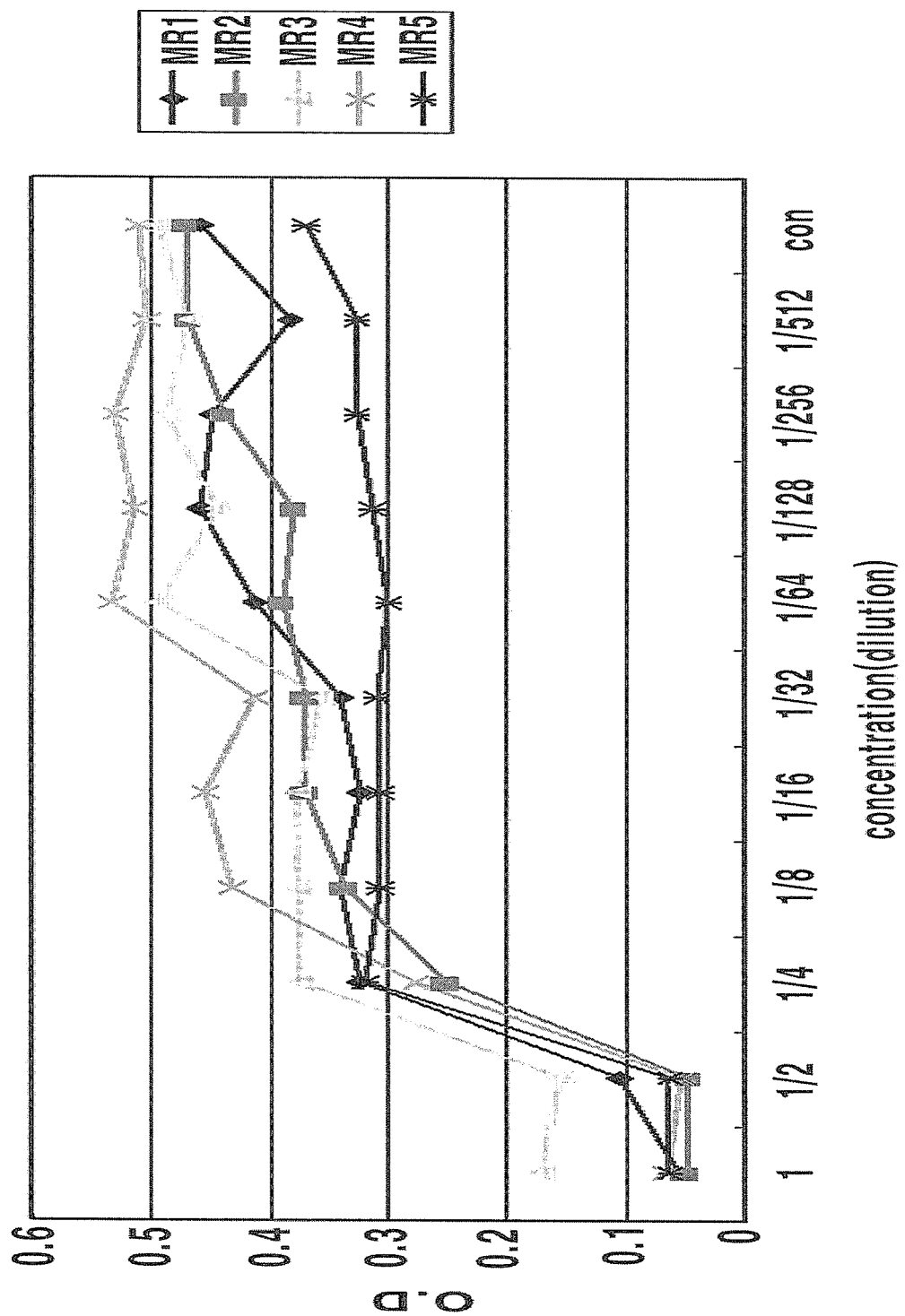
FIG. 6 is a graph illustrating the growth inhibition of MRSA 1, MRSA, 2, MRSA 3, MRSA 4, and MRSA 5 according to the diluted concentrations of the supernatant of *Bacillus amyloliquefaciens* K317 culture solution.
Figure 7:
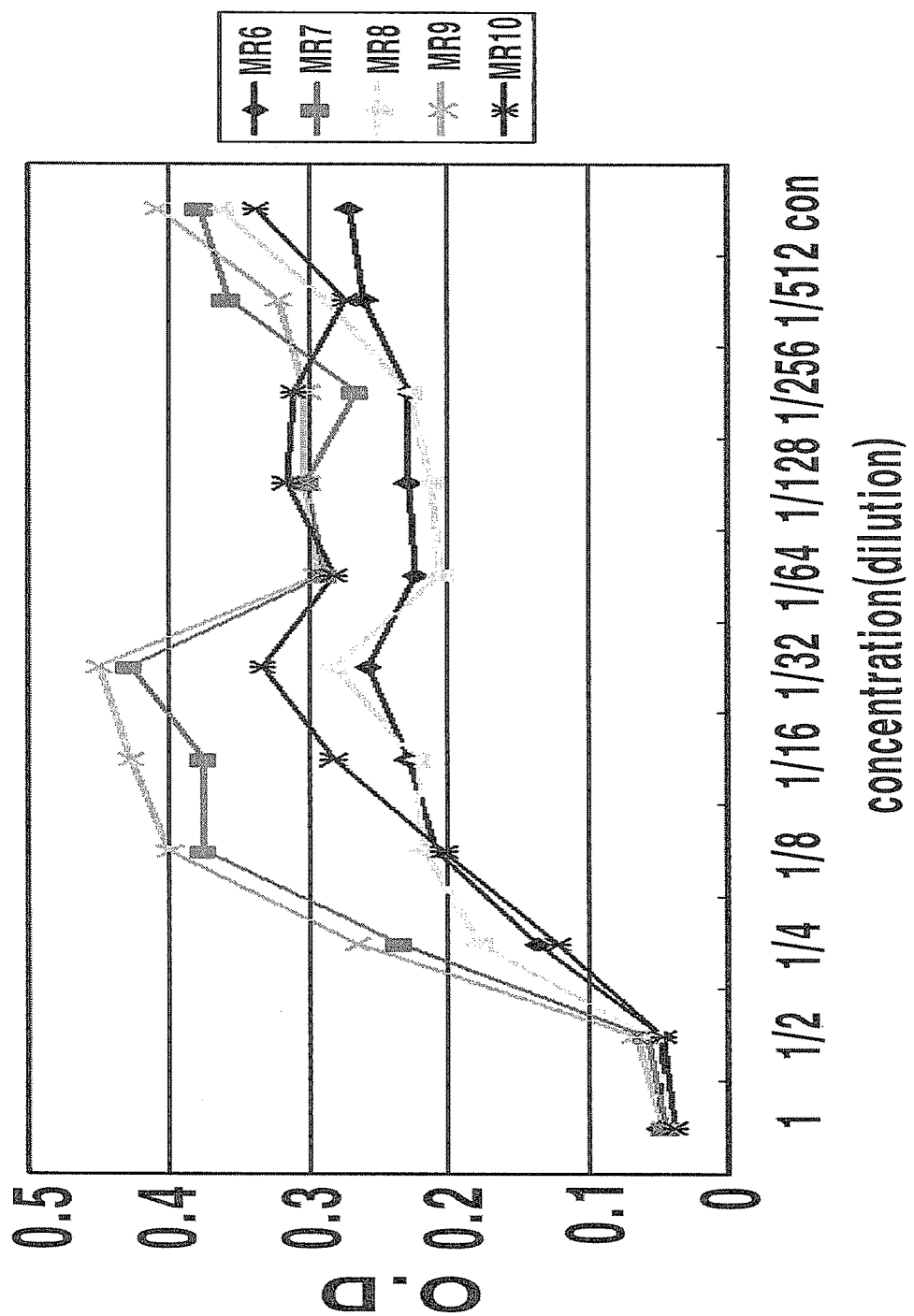
FIG. 7 is a graph illustrating the growth inhibition of MRSA 6, MRSA, 7, MRSA 8, MRSA 9, and MRSA 10 according to the diluted concentrations of the supernatant of *Bacillus amyloliquefaciens* K317 culture solution.
Figure 8:
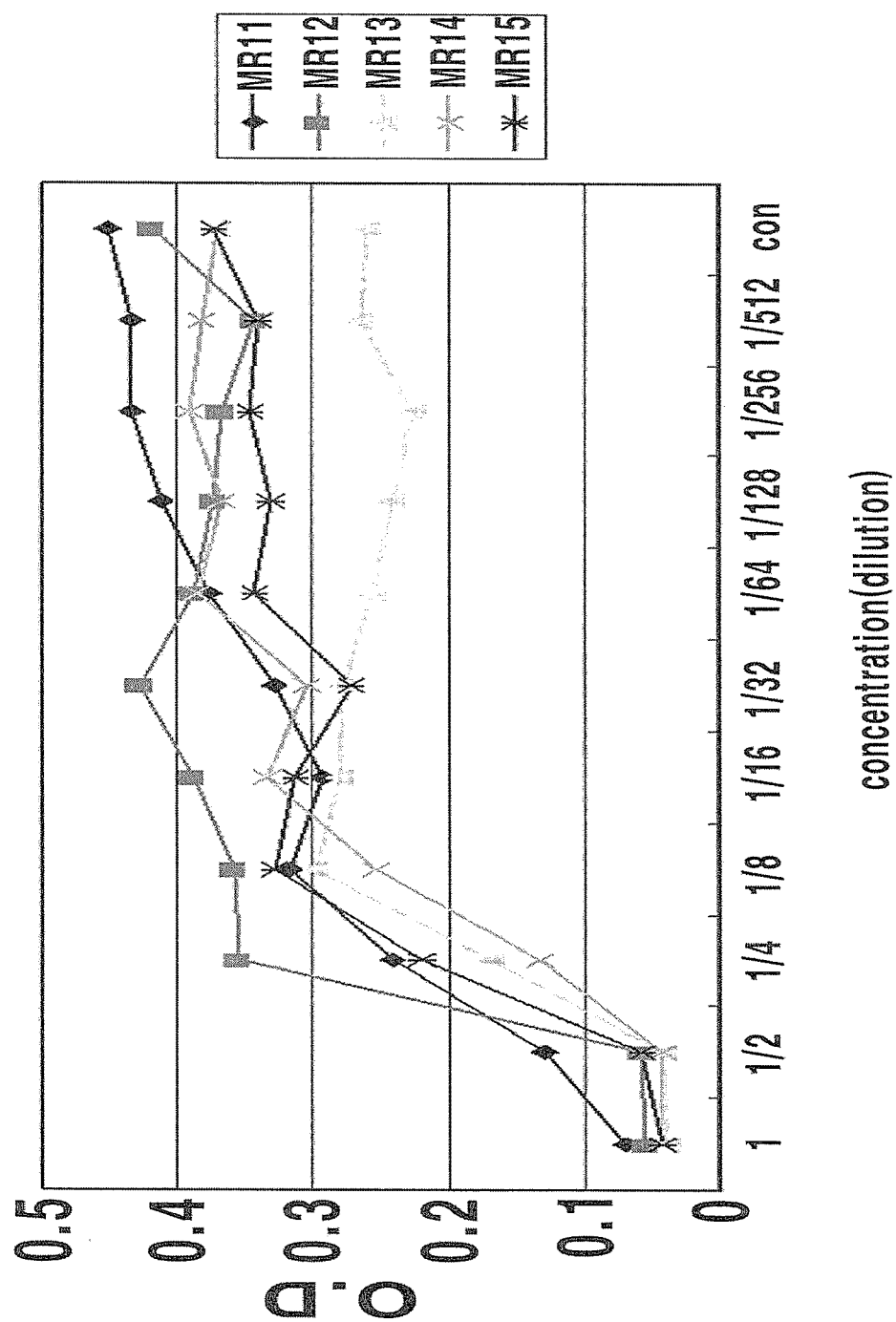
FIG. 8 is a graph illustrating the growth inhibition of MRSA 11, MRSA, 12, MRSA 13, MRSA 14, and MRSA 15 according to the diluted concentrations of the supernatant of *Bacillus amyloliquefaciens* K317 culture solution.
Figure 9:
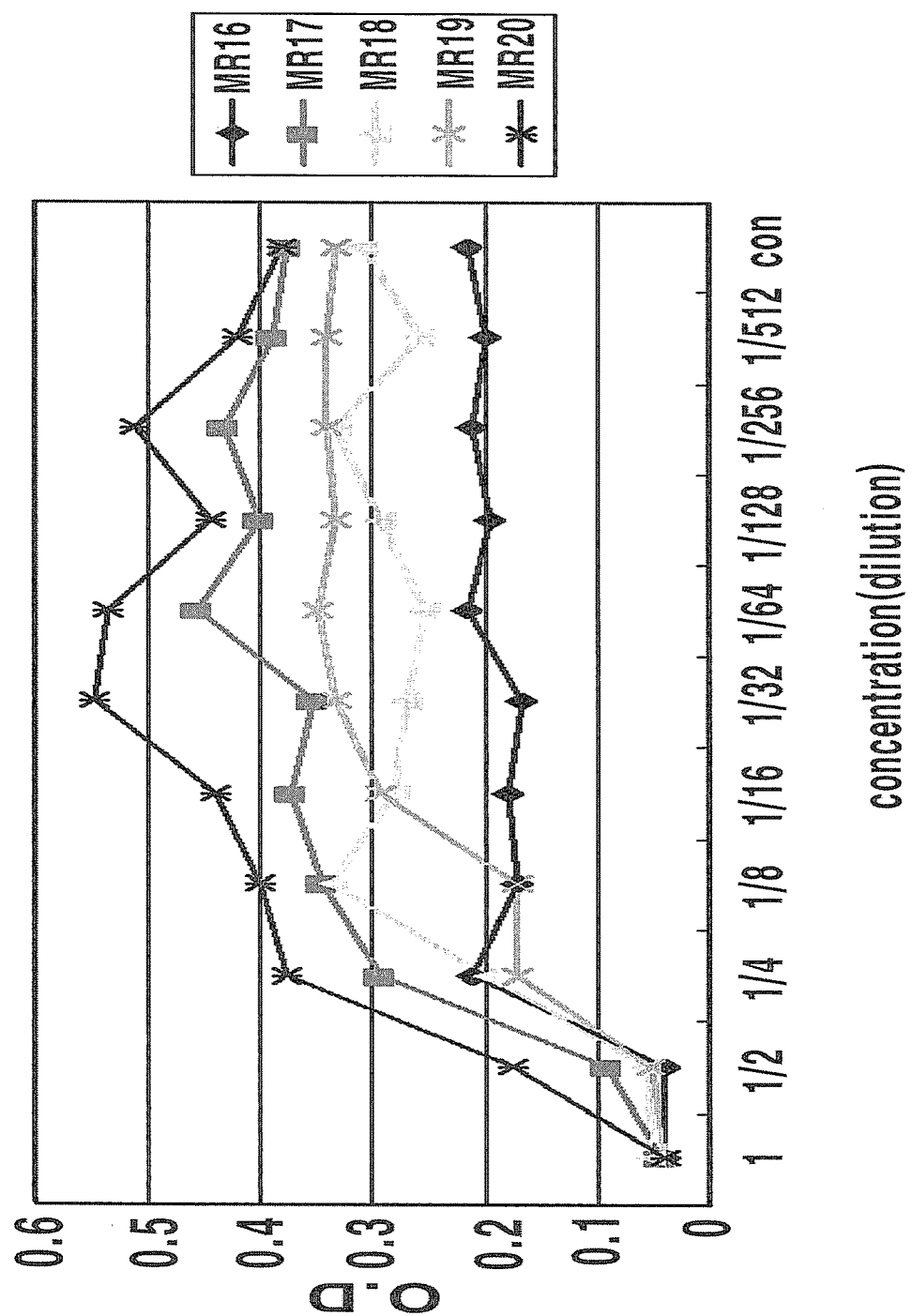
FIG. 9 is a graph illustrating the growth inhibition of MRSA 16, MRSA, 17, MRSA 18, MRSA 19, and MRSA 20 according to the diluted concentrations of the supernatant of *Bacillus amyloliquefaciens* K317 culture solution.
Figure 10:
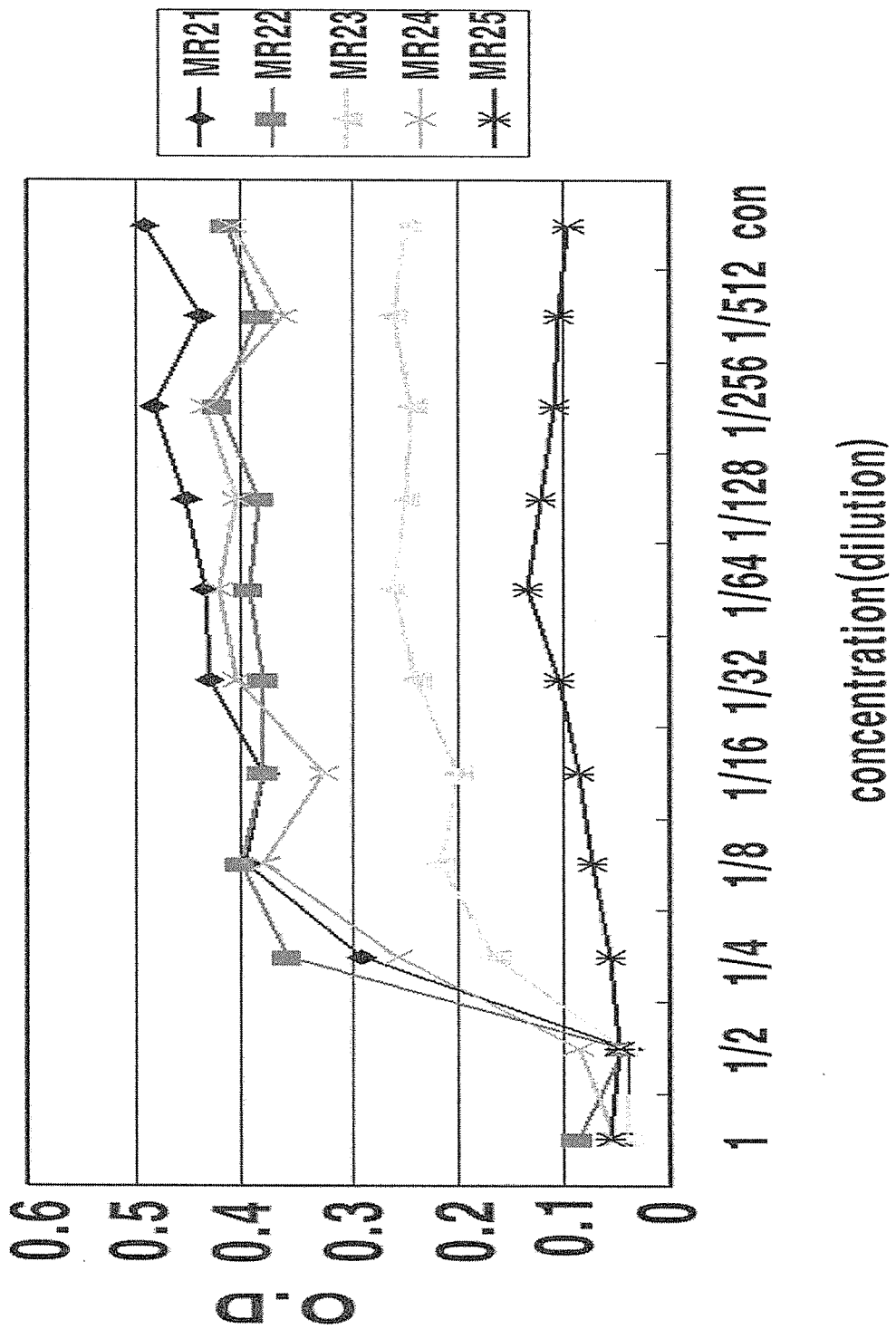
FIG. 10 is a graph illustrating the growth inhibition of MRSA 21, MRSA, 22, MRSA 23, MRSA 24, and MRSA 25 according to the diluted concentrations of the supernatant of *Bacillus amyloliquefaciens* K317 culture solution.
Figure 11:
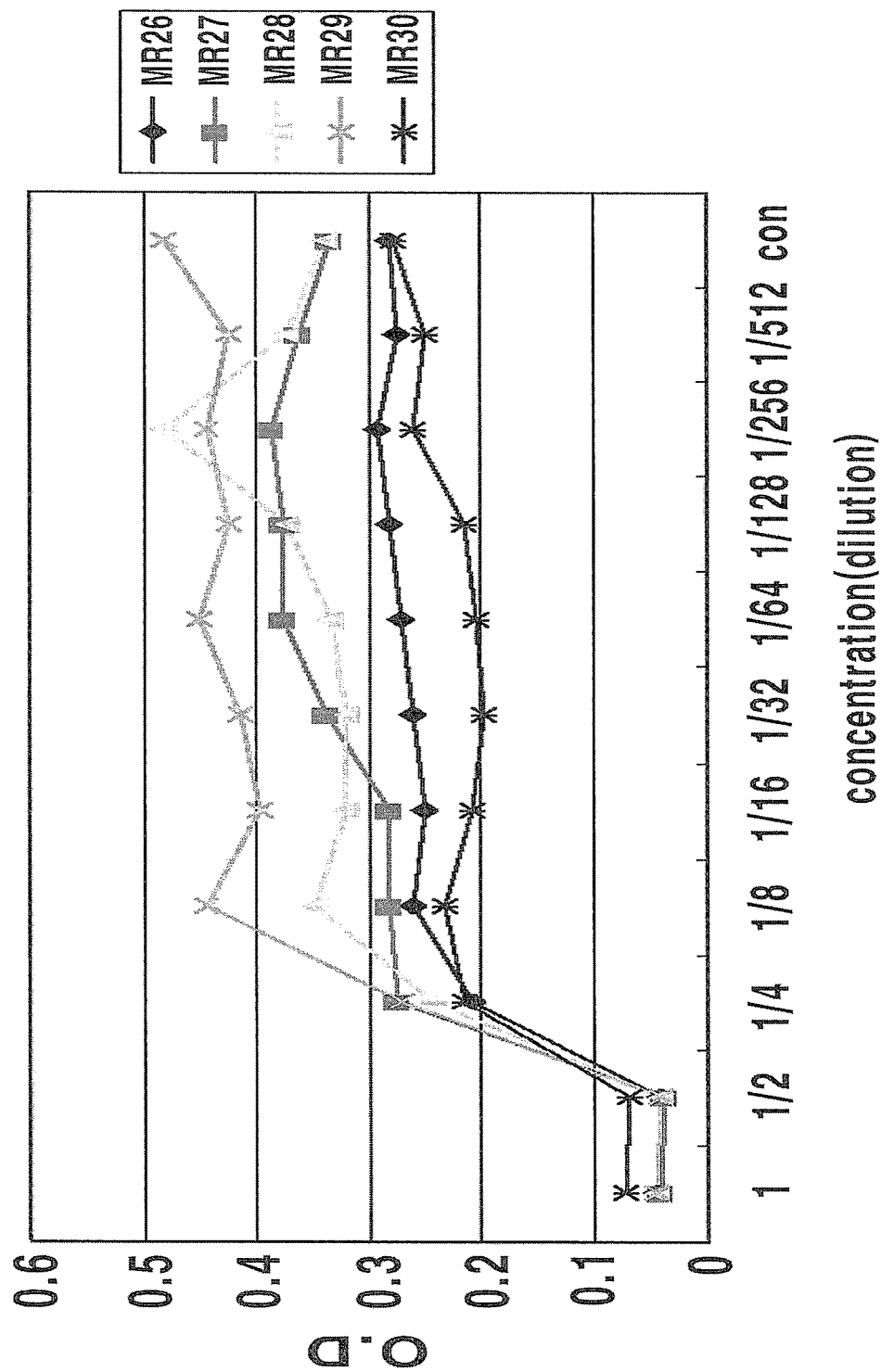
FIG. 11 is a graph illustrating the growth inhibition of MRSA 26, MRSA, 27, MRSA 28, MRSA 29, and MRSA 30 according to the diluted concentrations of the supernatant of *Bacillus amyloliquefaciens* K317 culture solution.

As a result, the growth of *Edwardsiella tarda, E. coli*, and *Staphylococcus epidermidis* were significantly suppressed in the undiluted supernatant or ½ diluted supernatant of *Bacillus amyloliquefaciens* K317 culture solution (see FIG. 5). In addition, the growth of most MRSA was suppressed in ¼ diluted supernatant of *Bacillus amyloliquefaciens* K317 culture solution. MRSA was hardly growing in the undiluted supernatant or ½ diluted supernatant, suggesting that the supernatant had very strong inhibitory effect (see FIGS. 6-12). From the results, it was confirmed that the supernatant of *Bacillus amyloliquefaciens* K317 culture solution of the present invention suppressed the growth of antibiotics-resistant pathogenic microorganism MRSA and enteropathogenic microorganisms effectively.

The present invention further provides an antibacterial metabolite isolated from the supernatant of the culture solution of *Bacillus amyloliquefaciens* K317.

The present inventors separated metabolites having the molecular weight of more than 10 kDa and less than 10 kDa from the supernatant of the culture solution, followed by examination of antibacterial activities on antibiotics-resistant pathogenic microorganisms. As a result, clear zone was observed in the paper disk treated with the metabolite having the molecular weight of more than 10 kDa (see FIG. 13) Therefore, it was confirmed that the metabolite having the molecular weight of more than 10 kDa separated from the culture supernatant inhibited effectively the growth of antibiotics-resistant pathogenic microorganism MRSA and enteropathogenic microorganisms.

The present invention also provides probiotics comprising the above strain, the culture supernatant or the antibacterial metabolite as an active ingredient.

As explained hereinbefore, the *Bacillus amyloliquefaciens* K317 strain, the culture supernatant thereof or the antibacterial metabolite isolated from the supernatant of the present invention had antibacterial activity against enteropathogenic microorganisms *Edwardsiella tarda, E. coli* and *Staphylococcus epidermidis*. Moreover, the strain of the present invention was isolated from the traditional safe fermented food Kimchi juice, so that it can be effectively used as non-toxic safe probiotics. The probiotics of the present invention can be applied to animals including cattle, food or animal feeds, in addition to medicines for animal and human.

The present invention also provides a composition for inhibiting the growth of antibiotics-resistant pathogenic microorganisms or enteropathogenic microorganisms which comprises the above strain, the culture supernatant or the antibacterial metabolite as an active ingredient.

The antibiotics-resistant pathogenic microorganism herein is preferably methicillin-resistant *Staphylococcus aureus* (MRSA), and the enteropathogenic microorganisms are preferably *Edwardsiella tarda, E. coli* and *Staphylococcus epidermidis*. The composition of the present invention can include, in addition to the *Bacillus amyloliquefaciens* K317 strain, the supernatant thereof or the antibacterial metabolite, one or more effective ingredients having the same or similar function.

The composition of the present invention can be administered orally or parenterally and be used in general forms of pharmaceutical formulation. The composition of the present invention can be prepared for oral or parenteral administration by mixing with generally used diluents or excipients such as fillers, extenders, binders, wetting agents, disintegrating agents and surfactant. Solid formulations for oral administration are tablets, pills, powders, granules and capsules. These solid formulations are prepared by mixing the *Bacillus amyloliquefaciens* K317 strain, the culture supernatant thereof or the antibacterial metabolite isolated from the same with one or more suitable excipients such as starch, calcium carbonate, sucrose or lactose, gelatin, etc. Liquid formulations for oral administration are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations, suppositories and injections. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61 (polyoxyethylene (4) sorbitan monostearate), cacao butter, laurin butter, glycerol, gelatin, etc.

The effective dosage of the composition can be determined according to weight, age, gender, health condition, diet, administration frequency, administration method, excretion and severity of a disease. The dosage of the *Bacillus amyloliquefaciens* K317 strain, the culture supernatant thereof or the antibacterial metabolite isolated from the same is 0.001~100 mg/kg per day and preferably 5~50 mg/kg per day, and administration frequency is once a day or preferably a few times a day.

The *Bacillus amyloliquefaciens* K317 strain, the culture supernatant thereof or the antibacterial metabolite isolated from the same of the present invention was evaluated to be a safe substance since its estimated $LD_{50}$ value was much greater than 1,000 mg/kg in mice, which was confirmed by acute toxicity assay with rats tested via oral administration.

The composition of the present invention can be treated independently or co-treated with surgery, hormone therapy, chemo-therapy and biological regulators, for the prevention and treatment of disease caused by pathogenic microorganisms such as MRSA and enteropathogenic microorganisms such as *Edwardsiella tarda, E. coli* and *Staphylococcus epidermidis*.

The present invention also provides health food for inhibiting the growth of antibiotics-resistant pathogenic microorganisms or enteropathogenic microorganisms comprising *Bacillus amyloliquefaciens* K317, the culture supernatant thereof or the antibacterial metabolite as an active ingredient.

The antibiotics-resistant pathogenic microorganism herein is preferably methicillin-resistant *Staphylococcus aureus* (MRSA), and the enteropathogenic microorganisms are preferably *Edwardsiella tarda, E. coli* and *Staphylococcus epidermidis*.

Health food containing the *Bacillus amyloliquefaciens* K317 strain, the culture supernatant thereof or the antibacterial metabolite isolated from the same of the present invention can be folk remedies for inhibiting the growth of pathogenic microorganisms which are exemplified by tea, jelly, soup, extract, beverages, etc, containing the *Bacillus amyloliquefaciens* K317 strain, the culture supernatant thereof or the antibacterial metabolite isolated from the same as an active ingredient. Health food for inhibiting the growth of antibiotics-resistant pathogenic microorganisms or enteropathogenic microorganisms of the present invention processed in various forms is safe without causing side effects in human, is excellent in inhibiting the growth of pathogenic microorganisms, and facilitates the administration and long-term storage.

The *Bacillus amyloliquefaciens* K317 strain, the culture supernatant thereof or the antibacterial metabolite isolated from the same of the present invention can be used for health food to suppress the growth of pathogenic microorganisms. In that case, the *Bacillus amyloliquefaciens* K317 strain, the culture supernatant thereof or the antibacterial metabolite isolated from the same can be added as it is or as mixed with other food components according to the conventional method. The mixing ratio of active ingredients can be regulated according to the purpose of use (prevention, health enhancement or treatment). In general, to produce health food or beverages, the *Bacillus amyloliquefaciens* K317 strain, the culture supernatant thereof or the antibacterial metabolite isolated from the same is added preferably by up to 15 weight part and more preferably by up to weight part for 100 weight part of the raw material. However, if long term administration is required for health and hygiene or regulating health condition, the content can be lower than the above but higher content can be accepted as well since the *Bacillus amyloliquefaciens* K317 strain, the culture supernatant thereof or the antibacterial metabolite isolated from the same has been proved to be very safe.

The food herein is not limited. For example, the *Bacillus amyloliquefaciens* K317 strain, the culture supernatant thereof or the antibacterial metabolite isolated from the same can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The composition for health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and sugar alcohols such as xilytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01-0.04 g and more preferably 0.02-0.03 g in 100 g of the *Bacillus amyloliquefaciens* K317 strain, the culture supernatant thereof or the antibacterial metabolite isolated from the same.

In addition to the ingredients mentioned above, health food containing the *Bacillus amyloliquefaciens* K317 strain, the culture supernatant thereof or the antibacterial metabolite isolated from the same of the present invention can include in variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. Health food containing the *Bacillus amyloliquefaciens* K317 strain, the culture supernatant thereof or the antibacterial metabolite isolated from the same can also include natural fruit juice, fruit beverages and/or fruit flesh addable to vegetable beverages. All the mentioned ingredients can be added singly or together. The mixing ratio of those ingredients does not matter in fact, but in general, each can be added by 001-0.1 weight part per 100 weight part of the *Bacillus amyloliquefaciens* K317 strain, the culture supernatant thereof or the antibacterial metabolite isolated from the same of the present invention.

The present invention also provides a feed additive for inhibiting the growth of antibiotics-resistant pathogenic microorganisms or enteropathogenic microorganisms comprising *Bacillus amyloliquefaciens* K317, the culture supernatant thereof or the antibacterial metabolite as an active ingredient.

The antibiotics-resistant pathogenic microorganism herein is preferably methicillin-resistant *Staphylococcus aureus* (MRSA), and the enteropathogenic microorganisms are preferably *Edwardsiella tarda, E. coli* and *Staphylococcus epidermidis*.

The feed additive of the present invention can be added to animal feeds. The feed additive of the invention contains *Bacillus amyloliquefaciens* K317 strain, the culture supernatant thereof or the antibacterial metabolite isolated from the same by 1-20 weight part, and more preferably 10-20 weight part for 100 weight part of the conventional animal feed. The feed additive of the present invention is expected to have antibacterial effect and growth inhibiting effect on MRSA and such enteropathogenic microorganisms as *Edwardsiella tarda, E. coli* and *Staphylococcus epidermidis* (see FIGS. 4-12).

MODE FOR INVENTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Separation of the Microorganism having Antibacterial Activity

To separate the microorganism having antibacterial activity against MRSA (methicillin-resistant *Staphylococuus aureus*), the antibiotics-resistant pathogenic microorganism, Kimchi juice properly diluted was smeared on the tryptic soy agar (TSA, Difco) medium pre-smeared with MRSA, followed by culture at 37° C. for 48 hours. Upon completion of the culture, tens of colonies exhibiting clear zone were selected (FIG. 1). The Kimchi was prepared as follows; cleaned Chinese cabbage, cut it into two equal pieces crosswise, soaked them in approximately 7% (w/w) salt water, salted down at room temperature (approximately 25° C.) for 14 hours, washed the salted cabbages with tap water three times, and dehydrated them for 2 hours; and radish (cut into 4×4 cm), green onion and other ingredients were added to the prepared cabbages. The other ingredients were those: salted fish prepared by mixing pickled oysters, salted anchovies, salted shrimps and other salted fishes, and garlic, ginger, hot red pepper powder, glutinous rice flour, and sugar. They were all mixed and stored at 5° C., resulting in the fermented Kimchi. The selected colonies were transferred onto fresh TSA medium and cultured 3 times, leading to pure isolation. The isolated microorganism strain was stored in 20% glycerol at −80° C.

Example 2

Identification of the Separated K317 Strain

The K317 strain finally selected in Example 1 was identified by morphological classification method and the newest molecular systematic method. The K317 strain was grown best when it was cultured on TSA (Tryptic Soy Agar, Difco) medium at 30-37° C. Its morphological characteristics were investigated by Gram staining, and as a result, the strain was confirmed to be a Gram positive *bacillus*. The strain was finally identified as *Bacillus amyloliquefaciens* by 16S rRNA nucleotide sequencing. The nucleotide sequencing and analysis were as follows. To extract DNA, the cultured cells were resuspended in 100 µl of STES buffer (0.4 M NaCl, 0.2 M Tris-HCl (pH 7.6), 0.01 M EDTA, 1% SDS). Glass beads were added to the sample, followed by lysis for 5 minutes with TOMY (micro tube mixer MT-360) to elute cytoplasm. The eluent was suspended in 200 µl of TE buffer (pH 8.0) and 200 µl of phenol/chloroform, followed by centrifugation. 5 µl of RNase A was treated to the supernatant, followed by reaction for one hour at 37° C. 200 µl of chloroform was added thereto, followed by centrifugation at 12,000 rpm for 5 minutes. The supernatant was washed with ethanol twice and then dried (vacuum dry: SpeedVac). The recovered DNA was dissolved in sterilized distilled water and stored. For PCR to amplify 16S rDNA, universal primer comprising PCR premix (Bioneer, Korea), forward primer (5'-GAG TTT GAT CCT GGC TCA G-3': SEQ. ID. NO: 1) and reverse primer (5'-GGT TAC CTT GTT ACG ACT T-3': SEQ. ID. NO: 2) was used. The final volume of the reaction mixture for PCR was 20 µl and PCR was performed as follows; denaturation at 94° C. for 1 minute, annealing at 50° C. for 1 minute, DNA polymerization at 72° C. for 1 minute and 50 seconds (30 cycles).

Figure 2:
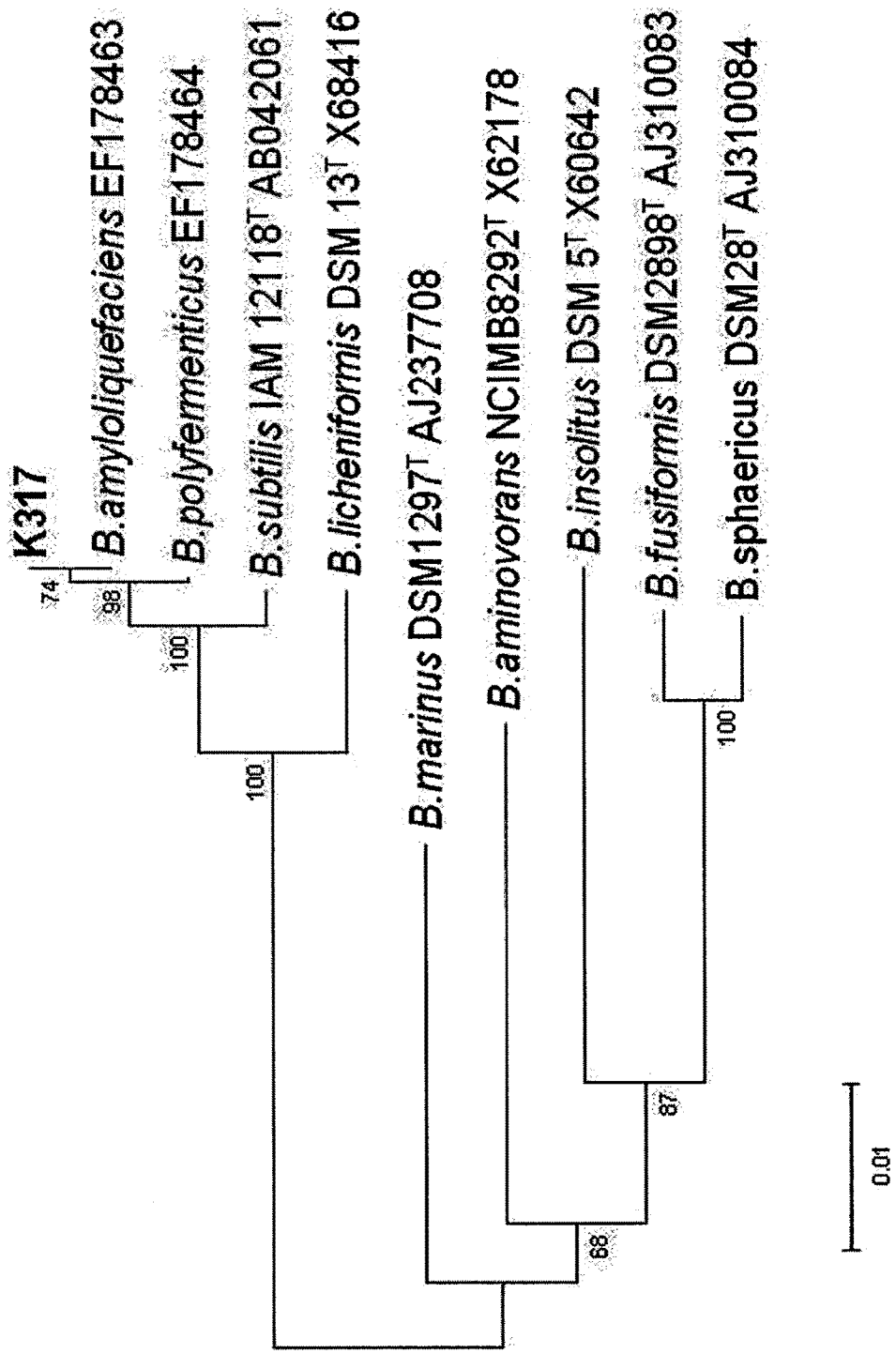
FIG. 2 is a phylogenetic tree based on 16S rRNA sequence showing the relation of the K317 strain of the present invention and the conventional strains.

Nucleotide sequencing (SEQ. ID. NO: 3) and systematic analysis of the amplified DNA was performed according to the method of Chang, et al (Chang et al., *Int. J. Syst. Evol. Microbiol.* 52: 377-381, 2002) (FIG. 2 and Table 1). The identified K317 strain was deposited at Korean Collection for Type Cultures (KCTC), Korea Research Institute of Bioscience and Biotechnology (KRIBB) located at 52, Eoeun-Dong, Yuseong-Gu, Daejeon, Korea, on Dec. 4, 2006 (Accession No: KCTC 11042BP).

TABLE 1

|  | 1 | 2 | 3 | 4 | 5 | 6 | 7 | 8 | 9 | 10 |
|---|---|---|---|---|---|---|---|---|---|---|
| 1. K317 | 100 | | | | | | | | | |
| 2. B. polyfementlcus | 99.93 | 100 | | | | | | | | |
| 3. B. amyloliquefacians | 100 | 99.93 | 100 | | | | | | | |
| 4. B. subtilis IAM1118 | 99.48 | 99.55 | 99.48 | 100 | | | | | | |
| 5. B. licheniformis DSM13 | 97.91 | 97.99 | 97.91 | 98.14 | 100 | | | | | |
| 6. B. marinus DSM1297 | 92.17 | 92.17 | 92.17 | 92.17 | 92.61 | 100 | | | | |
| 7. B. fusiformis DSM2898 | 91.35 | 91.42 | 91.35 | 91.5 | 91.5 | 92.55 | 100 | | | |
| 8. B. sphaericus DSM28 | 91.13 | 91.2 | 91.13 | 91.42 | 91.42 | 93 | 98.96 | 100 | | |
| 9. B. aminovorans NCIMB8292 | 91.91 | 91.91 | 91.91 | 92.06 | 91.99 | 94.32 | 92.82 | 93.12 | 100 | |
| 10. B. insolitus DSM5 | 91.45 | 91.53 | 91.45 | 91.68 | 91.76 | 94.08 | 94.24 | 94.09 | 94.08 | 100 |

Example 3

Inhibiting Capacity of *Bacillus amyloliquefaciens* K317 on the Growth of Pathogenic Microorganisms To investigate the inhibiting activity of the K317 strain identified in Example 2 on the growth of pathogenic microorganisms, following experiment was performed. The K317 strain was cultured on TSA medium at 37° C. for 24 hours. Enteropathogenic microorganisms herein were *Salmonella typhimurium*, *Edwardsiella tarda*, *E. coli* and *Staphylococcus epidermidis* distributed from Korean Collection for Type Cultures (KCTC), Korea Research Institute of Bioscience and Biotechnology (KRIBB). And 30 strains of MRSA distributed from Culture Collection of Antimicrobial Resistant Microbes, Seoul Women's University, Seoul, Korea, were used as antibiotics-resistant bacteria. For the pathogenic bacteria growth inhibition test, the strains were cultured on Mueller Hinton media (MH, Difco, USA) at 37° C. for 48 hours. Then, the formation of clear zone was observed. The present inventors smeared live pathogenic microorganisms each cultured on TSA (Tryptic Soy Agar, Difco) medium on MH medium at the density of $10^{6-7}$ CFU/ml. The K317 strain was streaked on the medium and cultured.

Figure 3:
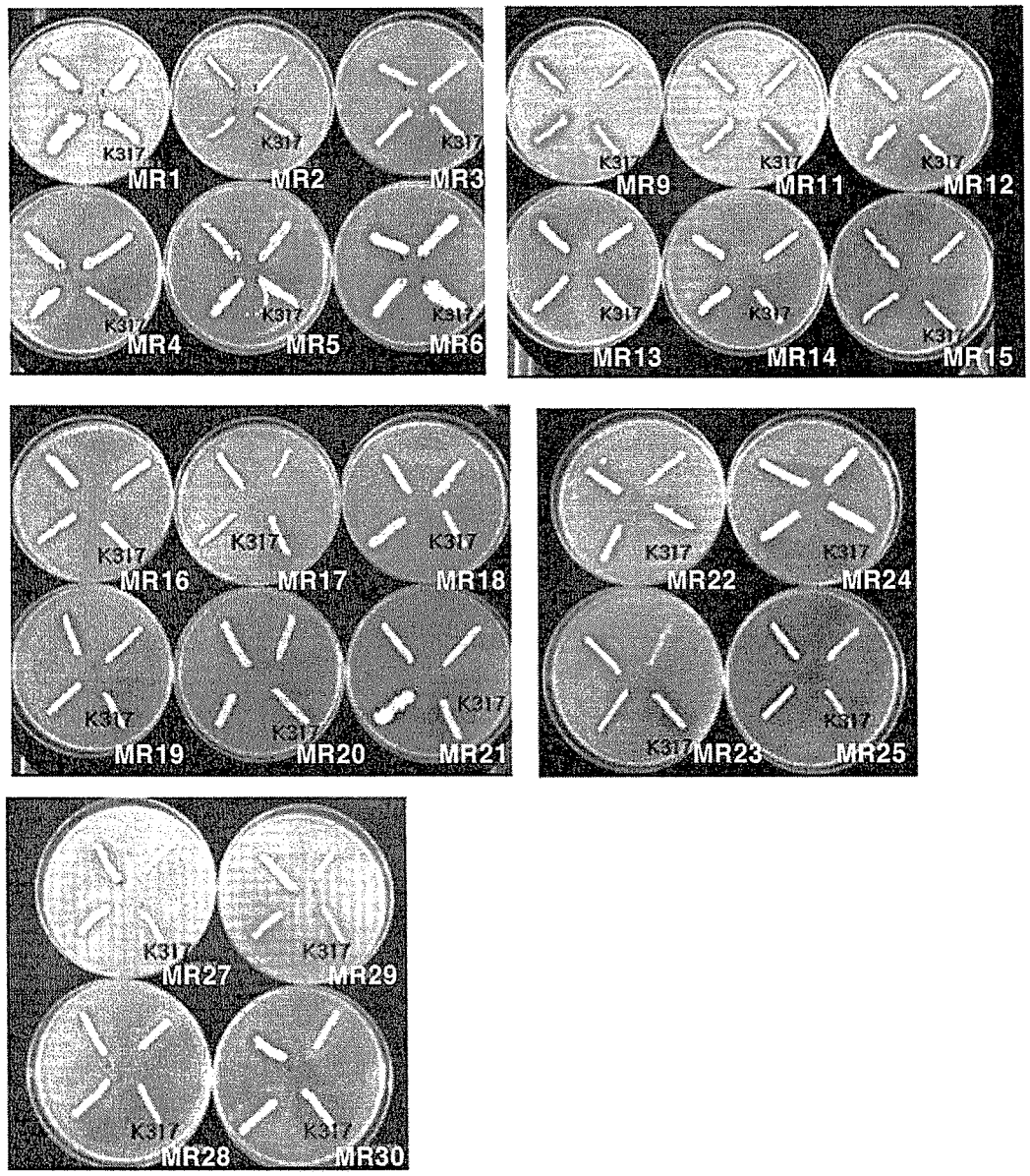
FIG. 3 illustrates the antibacterial activity of *Bacillus amyloliquefaciens* K317 against MRSA (methicillin-resistant *Staphylococcus aureus*) 30.

As a result, clear zones were observed around pathogenic microorganisms and MRSA strains after the culture, suggesting that the growth of those pathogenic microorganisms and MRSA strains were suppressed (FIG. 3).

The inhibiting activity of the K317 strain on the growth of 2 MRSA strains (#1 and #6) presented as yellow colonies was investigated by mixed culture. The concentrations of K317 and MRSA were equally adjusted to $10^{6-7}$ CFU/ml and mixed together at the ratio of 1:1 (v/v), followed by mixed culture in MH liquid medium at 37° C. for 24 hours. The culture was diluted in PBS (Phosphate-Buffered Saline, Bioneer, Korea), smeared on TSA medium and measured the number of live cells.

Figure 4:
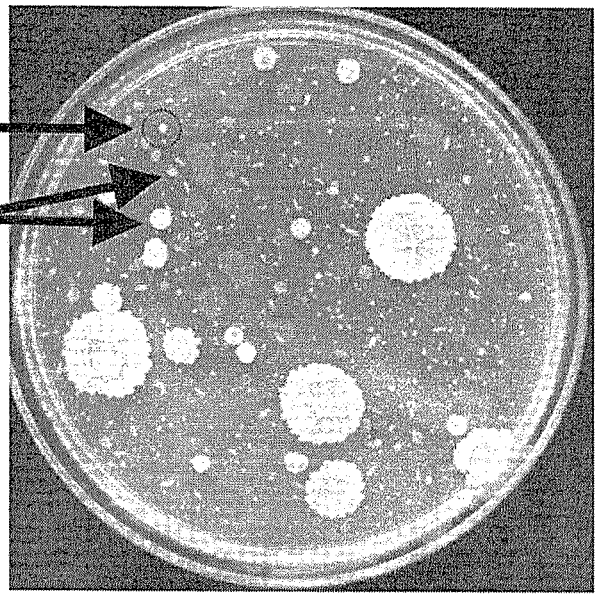
FIG. 4 illustrates the growth inhibition observed after co-culture of *Bacillus amyloliquefaciens* K317 and MRSA.
Figure 4:
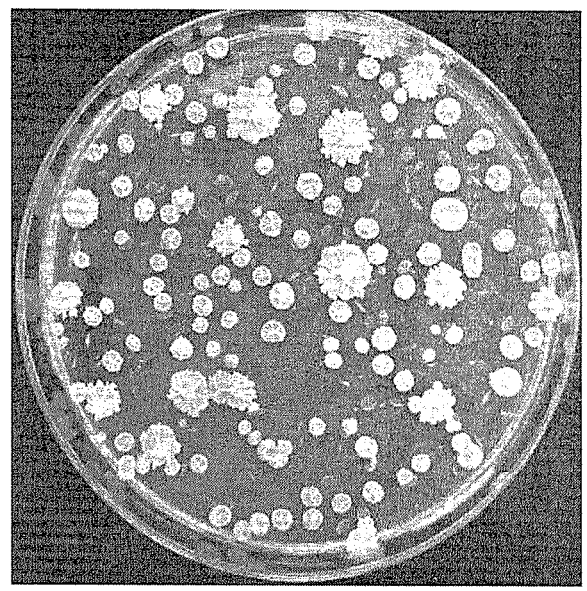

As a result, no colonies of MRSA, which was $10^{6-7}$ CFU/ml before the mixed culture, were found after 24 hours of the mixed culture with K317 (FIG. 4). The above result indicated that the K317 strain had excellent inhibiting activity on the growth of the MRSA strain.

Example 4

Growth Inhibition Test Using the Culture Solution of *Bacillus amyloliquefaciens* K317

K317 strain was cultured in MH liquid medium at 37° C. for 24 hours and the cells were eliminated from the culture solution by using 0.2 μm membrane filter (Satorius, Germany). The supernatant only was used for the following experiment. The supernatant was diluted to 1/512 by using sterilized MH broth. Each of the strains, *Salmonella typhimurium, Edwardsiella tarda, E. coli, Staphylococcus epidermidis* and 30 kinds of MRSA was distributed in 96-well plate, to which diluted K317 supernatant was added at different concentrations, followed by culture 37° C. for 24 hours. $OD_{595}$ (optical density) was measured by using ELISA reader (Benchmark microplate reader, BIO-RAD, USA).

As a result, the growth of *Edwardsiella tarda, E. coli,* and *Staphylococcus epidermidis* was suppressed in the undiluted and ½ diluted supernatant of *Bacillus amyloliquefaciens* K317 culture solution (FIG. 5). The supernatant of *Bacillus amyloliquefaciens* K317 culture solution inhibited the growth of 30 kinds of MRSA even at ¼ diluted solution and in the undiluted and ½ diluted supernatant, 30 kinds of MRSA were hardly grown (FIGS. 6-11).

To make accurate growth inhibition curve, the present inventors diluted the K317 supernatant further to 1/32 fold and growth inhibition curves on MRSA #1 and MRSA #6 were made every 3 hours by the same manner as described above. The sterilized MH liquid medium where the strain was not cultured was used as a negative control and the medium where MRSA was cultured without addition of the K317 supernatant was used as a positive control.

Figure 12:
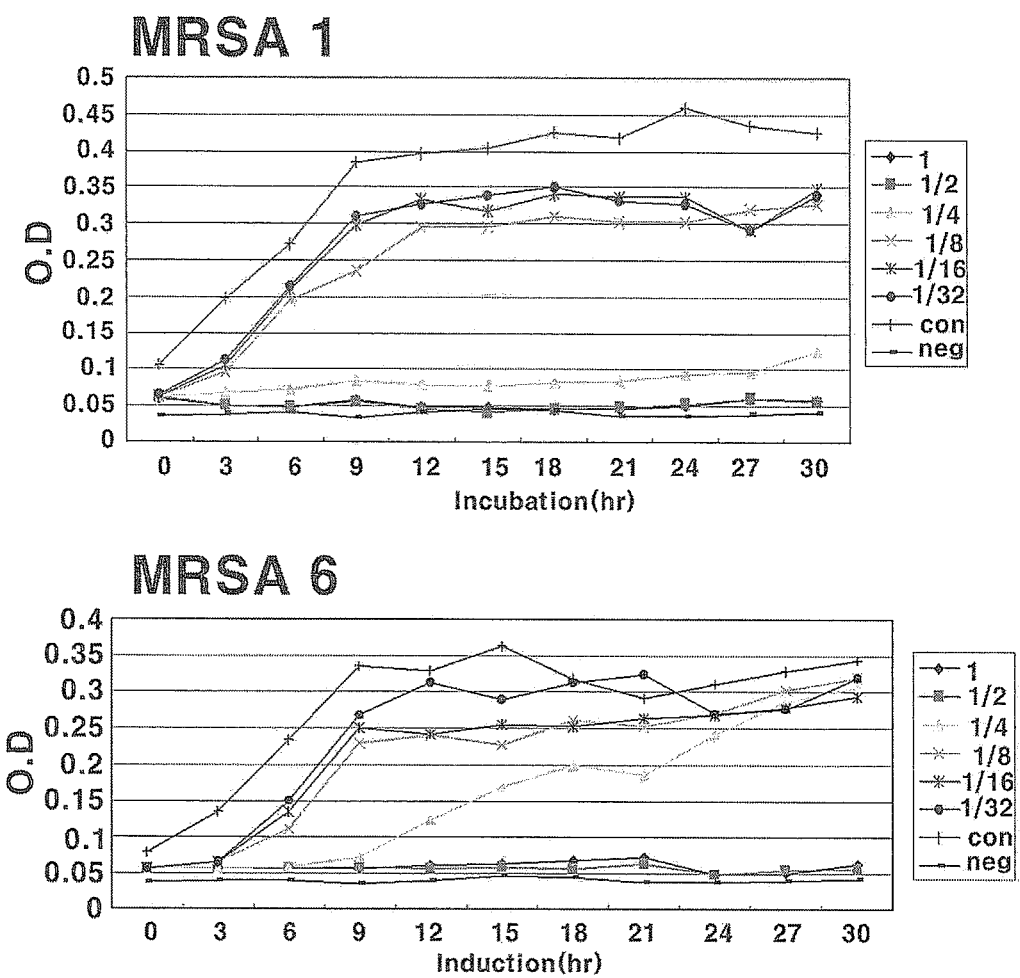
FIG. 12 is a graph illustrating the growth inhibition of MRSA 1 and MRSA 6 over the culture time and diluted concentrations of the supernatant of *Bacillus amyloliquefaciens* K317 culture solution.

As a result, the growth of MRSAs was suppressed in all the diluted supernatants and particularly MRSAs were not grown at all at the concentrations over ¼ fold dilution, particularly 1:1 and 1:½ dilutions, exhibiting the strong inhibitory effect (FIG. 12).

Example 5

Antibacterial Metabolites Produced by *Bacillus amyloliquefaciens* K317

Figure 13:
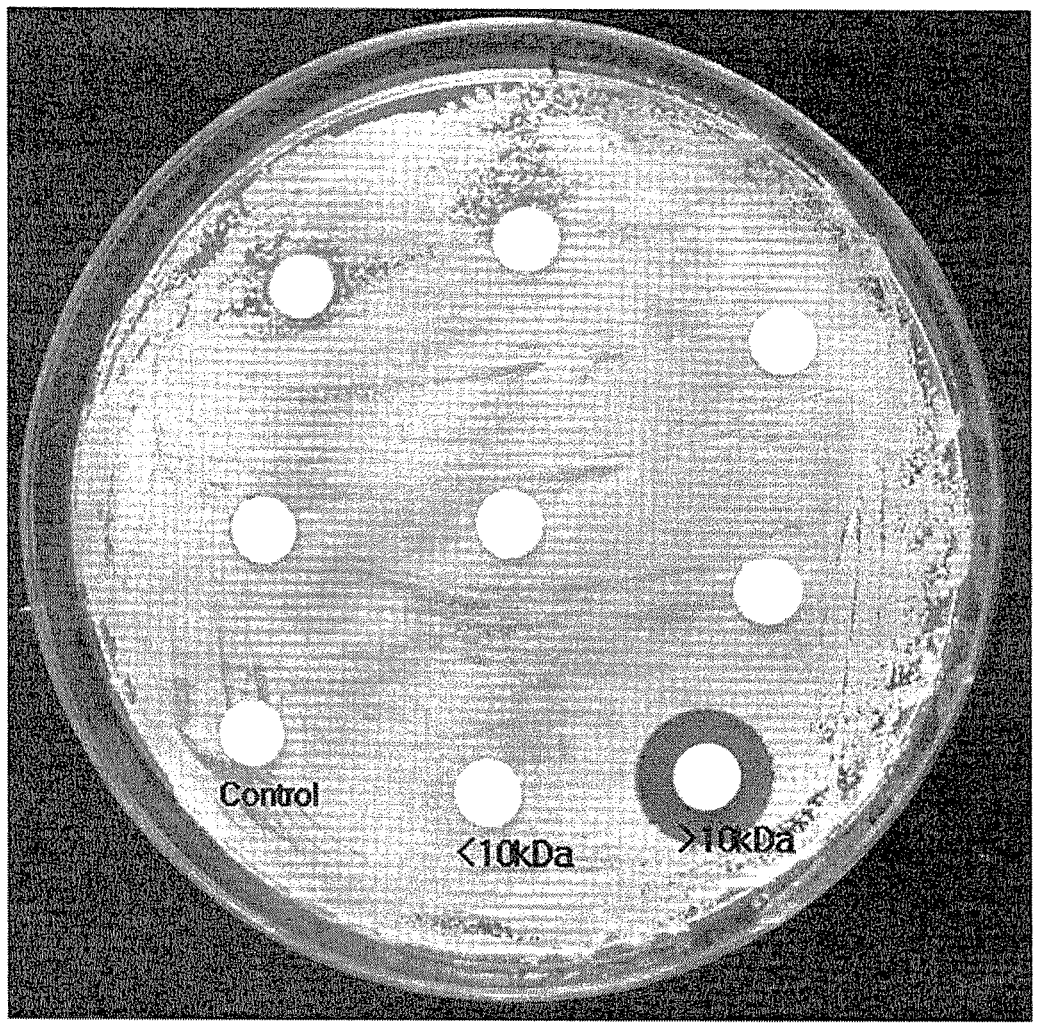
FIG. 13 illustrates the antibacterial capacity of the antibacterial metabolite in the supernatant of *Bacillus amyloliquefaciens* K317 culture solution.

K317 strain was cultured in 100 ml of TSB medium, and then the cells were eliminated by using 0.2 μm filter to prepare the supernatant. The supernatant was concentrated by centrifugation at 3,000×g using Centricon YM-10 (Milipore, USA). As a result, the metabolites of less than 10 kDa in molecular weight and more than 10 kDa in molecular weight were respectively obtained. Antibacterial activity of the metabolite in the culture solution sorted according to the molecular weight was measured by paper disc (diameter: 6 mm, Toyo Roshi Kaisha, Japan) method. 30 strains of MRSA were cultured on TSA (Tryptic Soy Agar, Difco) and the number of live cells was adjusted to $10^{6-7}$ CFU/ml, which were smeared on MH medium. Paper disc was placed on the medium, to which the materials separated by the centrifugation by molecular weight were dropped and absorbed thereon by 20 μl. After culturing thereof, clear zones were observed around the paper disc absorbing the materials of more than 10 kDa in molecular weight. Therefore, it was confirmed that an antibacterial material suppressing the growth of MRSA strains is included in the supernatant of K317 culture solution and the molecular weight of the material is at least 10 kDa (FIG. 13).

Example 6

Acute Toxicity Test

The following experiments were performed to see if the *Bacillus amyloliquefaciens* K317 strain, the culture supernatant thereof or the antibacterial metabolite isolated from the same of the present invention had acute toxicity in rats.

6-week old specific pathogen free (SPF) SD line rats were used in the tests for acute toxicity. The *Bacillus amyloliquefaciens* K317 strain, the culture supernatant thereof or the antibacterial metabolite isolated from the same of the present invention was suspended in 0.5% methyl cellulose solution and orally administered once to 2 rats per group at the dosage of 1 g/kg/15 ml.

Death, clinical symptoms, and weight change in rats were observed, hematological tests and biochemical tests of blood were performed, and any abnormal signs in the gastrointestinal organs of chest and abdomen were checked with eyes during autopsy.

The results showed that the *Bacillus amyloliquefaciens* K317 strain, the culture supernatant thereof or the antibacterial metabolite isolated from the same of the present invention did not cause any specific clinical symptoms, weight change, or death in rats. No change was observed in hematological tests, biochemical tests of blood, and autopsy.

The *Bacillus amyloliquefaciens* K317 strain, the culture supernatant thereof or the antibacterial metabolite isolated from the same of the present invention used in this experiment was evaluated to be a safe substance since it did not cause any toxic change in rats up to the level of 1,000 mg/kg and its estimated $LD_{50}$ value was much greater than 1,000 mg/kg in rats.

Manufacturing Example 1

Preparation of Food

Foods containing the *Bacillus amyloliquefaciens* K317 strain, the culture supernatant thereof or the antibacterial metabolite isolated from the same of the present invention were prepared as follows.

<1-1> Preparation of Spices

Health enhancing spices were prepared by mixing 0.2~10 weight % of the Bacillus amyloliquefaciens K317 strain.

<1-2> Preparation of Tomato Ketchup and Sauce

Health enhancing tomato ketchup and sauce were prepared by mixing 0.2~10 weight % of the supernatant of *Bacillus amyloliquefaciens* K317 culture solution with tomato ketchup and sauce according to the conventional method.

<1-3> Preparation of Flour Food 0.1-5.0 weight % of the antibacterial metabolite of the present invention was added to the flour. Health enhancing foods such as bread, cake, cookies, crackers and noodles were prepared with the flour mixture according to the conventional method.

<1-4> Preparation of Soups and Gravies 0.1-1.0 weight part of the supernatant of *Bacillus amyloliquefaciens* K317 culture solution was added to soups and gravies. Health enhancing meat products, soups and gravies were prepared with this mixture by the conventional method.

<1-5> Preparation of Ground Beef

Health enhancing ground beef was prepared by mixing 10 weight % of the supernatant of *Bacillus amyloliquefaciens* K317 culture solution with ground beef according to the conventional method.

<1-6> Preparation of Dairy Products 0.1-1.0 weight % of the antibacterial metabolite of the present invention was added to milk. Health enhancing dairy products such as yoghurt, butter and ice cream were prepared with the milk mixture according to the conventional method.

<1-7> Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The antibacterial metabolite of the present invention was concentrated under reduced pressure, spray-dried and pulverized to obtain 60-mesh dry powders.

Sun-Sik was prepared by mixing the dry powders of the grains, seeds and the antibacterial metabolite of the present invention according to the below ratio.

Grains (brown rice: 30 weight part, Yulmu: 15 weight part, barley: 20 weight part), Seeds (wild sesame: 7 weight part, black soybean: 8 weight part, black sesame: 7 weight part), Dry powders of the antibacterial metabolite of the present invention (1 weight part),

*Ganoderma lucidum* (0.5 weight part),

*Rehmannia glutinosa* (0.5 weight part)

Manufacturing Example 2

Preparation of Beverages

<2-1> Preparation of Carbonated Beverages

Sugar (5~10%), citric acid (0.05~0.3%), caramel (0.005~0.02%), vitamin C (0.1~1%) and the antibacterial metabolite of the present invention were all mixed, to which purified water (79~94%) was added to make syrup. The syrup was sterilized at 85~98° C. for 20~180 seconds and then mixed with cold water at the ratio of 1:4. Carbonated beverages containing the antibacterial metabolite of the present invention were prepared by adding carbon dioxide (0.5~0.82%) to the mixture.

<2-2> Preparation of Health Beverages

The supernatant of *Bacillus amyloliquefaciens* K317 culture solution was mixed with liquid fructose (0.5%), oligosaccharide (2%), sugar (2%), salt (0.5%), and water (75%). After mixing completely, the mixture was sterilized instantly and filled small containers such as glass bottles, pet bottles, etc, to prepare health beverages.

<2-3> Preparation of Vegetable Juice

Health enhancing vegetable juice was prepared by adding 0.5 g of the supernatant of *Bacillus amyloliquefaciens* K317 culture solution to 1,000 ml of tomato or carrot juice according to the conventional method.

<2-4> Preparation of Fruit Juice

Health enhancing fruit juice was prepared by adding 0.1 g of the supernatant of *Bacillus amyloliquefaciens* K317 culture solution to 1,000 ml of apple or grape juice according to the conventional method.

Manufacturing Example 3

Preparation of Feeds

<3-1> Purified Feeds for Growing Pigs up to 50 kg

| | | |
|---|---|---|
| a) | Crude protein | at least 16 weight %, |
| | Lysine | at least 0.8 weight %, |
| | Crude lipid | up to 8 weight %, |
| | Crude fiber | up to 6 weight %, |
| | Starch | at least 33 weight %, |
| | Calcium | at least 0.7 weight %, |
| | Phosphate | at least 0.5 weight %, |
| | Sodium | at least 0.15 weight %, |
| b) | Copper | at least 20 mg, |
| | Zinc | at least 50 mg, |
| | Vitamin A | at least 4,000 IU, |
| | Vitamin D | at least 500 IU, |
| C) | Supernatant of *Bacillus amyloliquefaciens* K-317 culture solution | 0.02-20 ppm. |

<3-2> Milk Replacement Feeds for Growing Calves at Least 80 kg

| | | |
|---|---|---|
| a) | Crude protein | at least 17 weight %, |
| | Lysine | at least 1.25 weight %, |
| | Crude lipid | 15~30 weight %, |
| | Crude fiber | up to 2 weight %, |
| | Crude ash | up to 10 weight %, |
| | Calcium | at least 0.9 weight %, |
| | Phosphate | at least 0.7 weight %, |
| | Sodium | at least 0.2 weight %, |
| | Magnesium | at least 0.13 weight %, |
| | Powdered milk | at least 25 weight %, |
| b) | Copper | up to 15 mg, |
| | Vitamin A | at least 8,000 IU, |
| | Vitamin D | at least 1,000 IU, |
| | Vitamin E | at least 20 mg, |
| c) | Supernatant of *Bacillus amyloliquefaciens* K-317 culture solution | 0.02~20 ppm. |

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A pharmaceutical formulation comprising:
   a) one or more suitable excipients selected from the group consisting of:
   i) starch, calcium carbonate, sucrose, lactose, gelatin, or combinations thereof, ii) water, liquid paraffin, wetting agents, sweeteners, aromatics, preservatives, or combinations thereof and
   iii) propylene glycol, polyethylene glycol, vegetable oil, an injectable ester, polyoxyethylene (4) sorbitan monostearate, cacao butter, laurin butter, glycerol, gelatin, or combinations thereof; and
   b) an isolated *Bacillus amyloliquefaciens* K317 strain, a culture containing *Bacillus amylofiquefaciens* K317 strain or a culture supernatant containing a *Bacillus amylofiquefaciens* K317 strain, able to inhibit the growth of antibiotics-resistant pathogenic microorganisms or enteropathogenic microorganisms, wherein said strain is deposited at Korean Collection for Type Cultures under Accession No. KCTC 11042BP,
   wherein said pharmaceutical formulation is in a form selected from a pill, a tablet, a capsule or an emulsion.

2. The pharmaceutical formulation of claim 1, wherein the antibiotics-resistant pathogenic microorganism is methicillin resistant *Staphylococcus aureus* or wherein the enteropathogenic microorganism is *Edwardsiella tarda, E. coli*, or *Staphylococcus epidermidis*.

3. The pharmaceutical formulation of claim 1, wherein said pharmaceutical formulation is in the form of a pill.

4. The pharmaceutical formulation of claim 1, wherein said pharmaceutical formulation is in the form of a tablet.

5. The pharmaceutical formulation of claim 1, wherein said pharmaceutical formulation is in the form of a capsule.

6. The pharmaceutical formulation of claim 1, wherein said pharmaceutical formulation is in the form of an emulsion.

7. An animal feed comprising:
   a) crude protein, lysine, crude lipid, crude fiber, and
   b) an isolated *Bacillus amyloliquefaciens* K317 strain, a culture containing *Bacillus amylofiquefaciens* K317 strain or culture supernatant containing a *Bacillus amyloliquefaciens* K317 strain, able to inhibit the growth of antibiotics-resistant pathogenic microorganisms or enteropathogenic microorganisms;
   wherein said strain is deposited at Korean Collection for Type Cultures under Accession No. KCTC 11042BP,
   wherein said animal feed is in the form of a pill, a tablet, a capsule or an emulsion.

8. The animal feed of claim 7, wherein the antibiotics-resistant pathogenic microorganism is methicillin resistant *Staphylococcus aureus* or wherein the enteropathogenic microorganism is *Edwardsiella tarda, E. coli*, or *Staphylococcus epidermidis*.

9. The animal feed of claim 7, wherein said animal feed is in the form of a pill.

10. The animal feed of claim 7, wherein said animal feed is in the form of a tablet.

11. The animal feed of claim 7, wherein said animal feed is in the form of a capsule.

12. The animal feed of claim 7, wherein said animal feed is in the form of an emulsion.

13. The animal feed of claim 7, wherein said animal feed comprises 0.02-20 ppm of said an isolated *Bacillus amyloliquefaciens* K317 strain, a culture containing *Bacillus amylofiquefaciens* K317 strain or culture supernatant containing a *Bacillus amyloliquefaciens* K317 strain.

14. A method for inhibiting the growth of Methicillin-Resistant *Staphylococcus aureus* (MRSA), *Edwardsiella tarda, E. coli, Staphylococcus epidermis* or *Salmonella typhimurium*, comprising administering to a subject in need thereof, 0.001-100 mg/kg per day of the pharmaceutical formulation of claim 1.

15. The method of claim 14, wherein 5-50 mg/kg per day of the pharmaceutical formulation of claim 1 is administered to said subject in need thereof.

* * * * *